United States Patent
Ferry et al.

(10) Patent No.: US 9,491,412 B2
(45) Date of Patent: Nov. 8, 2016

(54) METHOD AND SYSTEM FOR DETERMINING QUALITY OF TUBES

(71) Applicant: ALSTOM Technology Ltd, Baden (CH)

(72) Inventors: Allan Gunn Ferry, Windsor, CT (US); Ronald Francis Konopacki, Suffield, CT (US); Robert F. Crocker, East Granby, CT (US)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 377 days.

(21) Appl. No.: 13/968,874

(22) Filed: Aug. 16, 2013

(65) Prior Publication Data

US 2014/0071267 A1 Mar. 13, 2014

Related U.S. Application Data

(60) Provisional application No. 61/700,750, filed on Sep. 13, 2012, provisional application No. 61/700,788, filed on Sep. 13, 2012.

(51) Int. Cl.
*H04N 7/18* (2006.01)
*G01N 21/88* (2006.01)
*G01N 21/952* (2006.01)

(52) U.S. Cl.
CPC ............ *H04N 7/18* (2013.01); *G01N 21/8851* (2013.01); *G01N 21/952* (2013.01)

(58) Field of Classification Search
CPC .............................. H04N 7/18; G01N 21/952
USPC .......................................................... 348/84
See application file for complete search history.

(56) References Cited

U.S. PATENT DOCUMENTS 5,099,115 A * 3/1992 Cruickshank ........ G03B 37/005
250/236
5,517,033 A * 5/1996 Krivanek .............. H01J 37/224
250/397

(Continued)

FOREIGN PATENT DOCUMENTS

CA    2 779 873        6/2011
CN    201285281 Y     8/2009

(Continued)

OTHER PUBLICATIONS

Office action issued from Chinese Patent Office dated Jan. 8, 2016 for CN Application No. 201310680451.X.

(Continued)

*Primary Examiner* — Jeffery Williams
(74) *Attorney, Agent, or Firm* — GE Global Patent Operation; Stephen G. Midgley

(57) ABSTRACT

Disclosed herein is a system having a first housing that includes an optically transparent substrate having a first side and a second side that is opposed to the first side, a camera disposed on the first side of the optically transparent substrate and a source of illumination. The source of illumination is disposed in a ring on the periphery of the first housing and located on the first side of the optically transparent substrate. The system further has a second housing having a circuit board that is operative to process the image captured by the camera, and a battery pack that is operative to supply electrical energy to the source of illumination and to power the circuit board.

16 Claims, 3 Drawing Sheets

(side view)

(56) References Cited

U.S. PATENT DOCUMENTS

| | | | |
|---|---|---|---|
| 5,793,468 A | 8/1998 | Shalon et al. | |
| 5,895,927 A * | 4/1999 | Brown | G01B 11/12 250/559.19 |
| 7,823,783 B2 * | 11/2010 | Gerst, III | G06K 7/10732 235/455 |
| 2004/0031337 A1 * | 2/2004 | Masaniello | F17D 5/02 73/865.8 |
| 2004/0128111 A1 * | 7/2004 | Lang | F22B 35/18 702/188 |
| 2004/0245338 A1 * | 12/2004 | Poloniewicz | G06K 7/10653 235/454 |
| 2010/0039640 A1 | 2/2010 | Colle | |
| 2011/0279828 A1 * | 11/2011 | Matsumoto | F22B 37/005 356/630 |

FOREIGN PATENT DOCUMENTS

| | | |
|---|---|---|
| CN | 102405394 A | 4/2012 |
| DE | 10 2007 05203 | 5/2009 |
| EP | 1 707 918 | 10/2006 |
| EP | 2 295 931 | 3/2011 |
| JP | 05-240619 A | 9/1993 |
| JP | H09-72726 | 3/1997 |
| JP | H10-38531 | 2/1998 |
| JP | H1038531 A * | 2/1998 ............ G01B 11/24 |
| JP | 11295028 A | 10/1999 |
| JP | 2000-009436 | 1/2000 |
| JP | 2001-283208 A | 10/2001 |
| JP | 2002-230523 | 8/2002 |
| JP | 2004-301619 A | 10/2004 |
| JP | 2005-134294 A | 5/2005 |
| JP | 2007-057344 | 3/2007 |
| JP | 2007-107927 A | 4/2007 |
| JP | 2008-170437 A | 7/2008 |
| JP | 2008-261679 | 10/2008 |
| JP | 2008-307601 A | 12/2008 |
| JP | 2009-115526 A | 5/2009 |
| JP | 2010-002232 A | 1/2010 |
| JP | 2010002232 A * | 1/2010 ............ G01B 11/24 |
| JP | 2010-101863 | 5/2010 |
| JP | WO 2011074261 A1 * | 6/2011 ............ B21C 37/06 |
| JP | 2012-154858 | 8/2012 |
| WO | 2011/138524 | 11/2011 |

OTHER PUBLICATIONS

Unofficial English translation of JP Office Action issued in connection with related JP Application No. 2013-190822 on Aug. 16, 2016.

* cited by examiner

Figure 1 (side view)

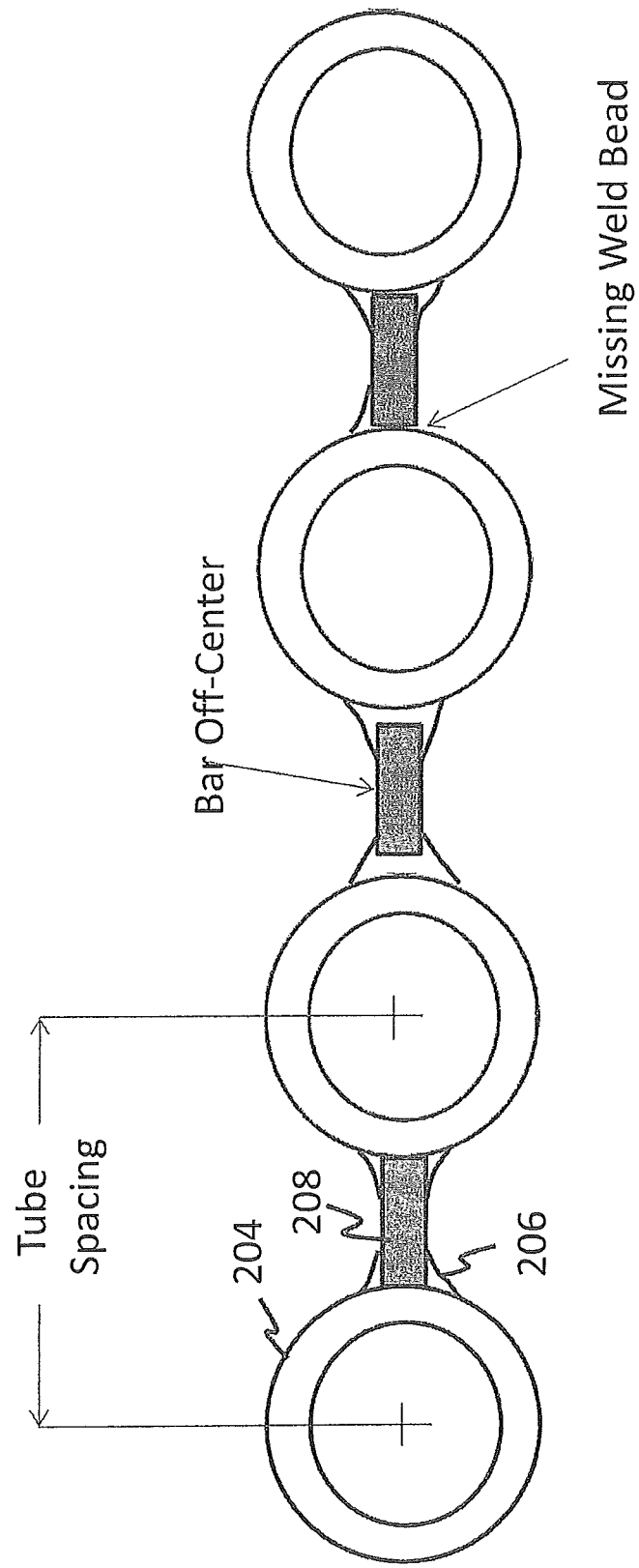

METHOD AND SYSTEM FOR DETERMINING QUALITY OF TUBES

CROSS-REFERENCE TO RELATED APPLICATIONS

This application claims priority to U.S. Provisional Application No. 61/700,750 filed Sep. 13, 2012, related U.S. Non-Provisional application Ser. No. 13/968,874 filed Aug. 16, 2013 titled, "METHOD AND SYSTEM FOR DETERMINING QUALITY OF TUBES", and to U.S. Provisional Application No. 61/700,788 filed Sep. 13, 2012 the disclosures of which are each hereby incorporated in their entirety.

TECHNICAL FIELD

This disclosure relates to a method and to a system for determining the quality of tubes. In particular, this disclosure relates to a hand held system that enables an automated method of determining the quality of tubes in boilers.

BACKGROUND

Boiler tube manufacturing uses a variety of different sized steel alloy tubes. In order to choose tubes for use in a boiler, it is desirable to know the diameter, wall thickness, composition of the material and/or the hardness of the tubes.

While material properties such as the composition can be identified using a handheld positive material identification device, the measurement of tube dimensions such as the diameter and the wall thickness often necessitate the use of hand-held devices such as vernier calipers, micrometers, and the like. This is a slow and error prone process.

Tubes are generally shipped in bundles and which are stored in a manufacturing location until desired. Random tests are made in an inspection laboratory located at the manufacturing location where the tubes are received. An inspector checks the tubes received against a master manifest, the purchase order and shipping documents, which give a description of the number and types of tubes that were shipped. Measurement of such a large number of tubes with hand-held devices is tedious and limits the number of tubes that are checked. All commonly used boiler regulations (e.g. ASME and EN) specify calculations that must be performed based on the measurements, with accepted criteria for each calculated value.

Typically, an inspection report is created after taking the cross-sectional measurements of a bent tube and performing the desired calculations. The inspection report details whether a particular bend sample failed or passed. This complete process may take several days if performed by hand in an inspection laboratory. It is therefore desirable to use a method that is quicker and that is less error prone.

SUMMARY

Disclosed herein is a system comprising a first housing comprising an optically transparent substrate having a first side and a second side that is opposed to the first side; a camera disposed on the first side of the optically transparent substrate; and a source of illumination; the source of illumination being disposed around the periphery of the first housing and located on the first side of the optically transparent substrate; where the source of illumination is operative to illuminate an object disposed on the second side of the optically transparent substrate; and where the camera is operative to capture an image of an object disposed upon the second side of the optically transparent substrate; and a second housing comprising a circuit board that is operative to process the image captured by the camera; and a battery pack that is operative to supply electrical energy to the source of illumination and to power the circuit board; where the second housing is fixedly attached to the first housing in a manner such that the system can be gripped in a single hand by a human being.

Disclosed herein too is a method comprising transporting a system to a stationary tube for purposes of inspecting the tube; where the system comprises a first housing comprising an optically transparent substrate having a first side and a second side that is opposed to the first side; a camera disposed upon the first side of the optically transparent substrate; and a source of illumination; the source of illumination being disposed in a ring on the periphery of the first housing and located on the first side of the optically transparent substrate; where the source of illumination is operative to illuminate the object disposed on the second side of the optically transparent substrate; and where the camera is operative to capture an image of an object disposed upon the second side of the optically transparent substrate; and a second housing comprising a circuit board that is operative to process images captured by the camera; and a battery pack that is operative to supply electrical energy to the source of illumination and to power the circuit board; where the second housing is fixedly attached to the first housing in a manner such that the system can be gripped in a single hand by a human being; contacting a cross-sectional area of a linear tube with the second side of the optically transparent substrate; where the cross-sectional area is taken perpendicular to an axis that passes through a center of mass of the cross-sectional area; imaging the cross-sectional area to obtain an image; transmitting the image to a microprocessor; segmenting the image into a plurality of segments; measuring an inner diameter and an outer diameter for each segment of the plurality of segments; and determining an inner diameter, an outer diameter, a center of mass, a wall thickness, an out of roundness and a flow area for the tube.

BRIEF DESCRIPTION OF THE DRAWINGS

FIG. 3 is a depiction of a cross-section of an exemplary water-wall whose dimensions and geometry are to be measured by the system disclosed herein.

DETAILED DESCRIPTION

Disclosed herein is a handheld portable system for measuring the various characteristics (dimensions and geometry) of a tube. The tube can be straight (without any bends) or bent. In an exemplary embodiment, the system is used for measuring the dimensions and geometry of a straight tube (also referred to herein as a linear tube). The system comprises a housing in which are disposed an optically transparent substrate, a source of illumination, and a camera. The camera is in operative communication with a microprocessor and a database. In one embodiment, the camera contains the microprocessor and thus communicates with the database. The database may be part of a computer and will hereinafter be referred to as a computer database. The system is light weight and can be transported by hand.

Disclosed herein too is a method that quickly and accurately inspects multiple tube cross-sections from a plurality of tubes, performs the desired measurements on each cross-section and calculates the values prescribed by ASME B31.1-2010 and EN 2 952-5. The method also includes generating an inspection report for each tube and saves the inspection data to a database. The method can be used on linear tubes or bent tubes. In an exemplary embodiment, the method is used on linear tubes. The method also involves storing, processing and transmitting the data in the computer database.

The method has significant advantages over other previously used methods that include the automatic collection of measurements by personnel who do not need any specific training. The measurement of tube geometry uses more measurement points and provides a more accurate and repeatable result than measurements made by hand with a vernier caliper and micrometer. Automatic transfer of the measured data from the camera to the microprocessor and to the database prevents transcription errors. Automatic performance of complex mathematical calculations can be conducted by shop personnel with little or no training. The method results in a reduction in hand calculation errors when compared with other traditional methods. Inspection reports can be obtained in several languages. Native speakers of different human languages can use the system and method in their preferred language. Inspection results can be obtained in under an hour (this includes tube preparation time such as cutting sections and polishing the cut ends to remove sharp edges).

Figure 1:
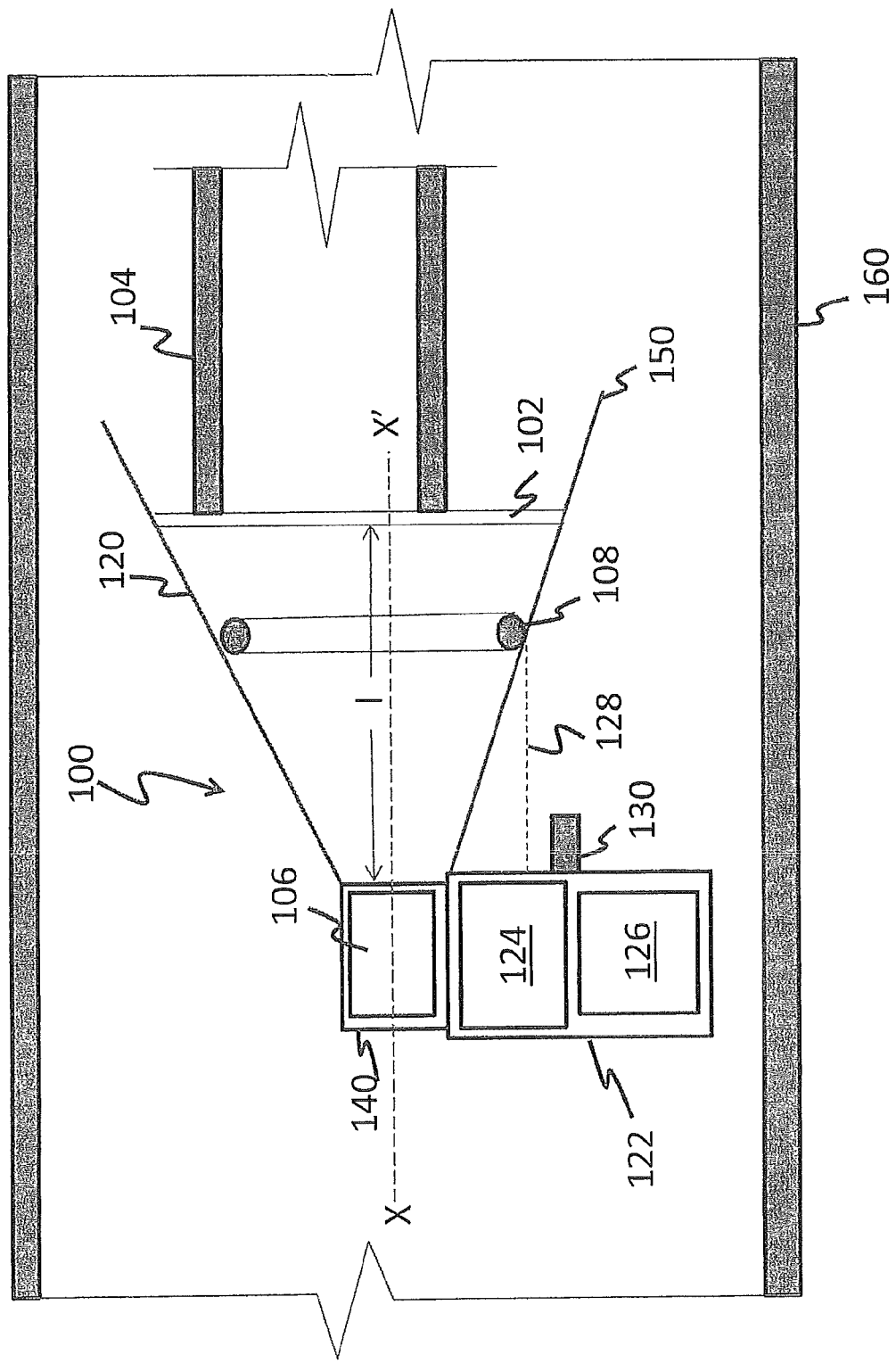
FIG. 1 is a depiction of an exemplary hand held, portable system that is used for measuring the dimensions and geometry of a tube.

FIG. 1 depicts a side view of a system 100 that is used for measuring the dimensional and geometric properties of a tube. The system 100 comprises a first housing 120 having a first end 140 and a second end 150 respectively that contains an optically transparent substrate 102, a camera 106 and a source of illumination 108, where the source of illumination 108 is disposed between the optically transparent substrate and the camera 106. The camera 106 is disposed in a first end 140 of the housing. The transparent substrate 102 is disposed towards the second end of the housing and has a first side and a second side, where the second side is opposed to the first side. The camera 106 may or may not contact the optically transparent substrate 102. A tube 104 whose dimensions and geometric properties are desired is brought into contact with the transparent substrate 102 as shown in the FIG. 1, and its cross-sectional area is illuminated by the source of illumination 108 and imaged by the camera 106.

The first housing 120 is fixedly attached to a second housing 122 that contains a circuit board 124 and a battery pack 126. The battery pack 126 and the circuit board 124 are in electrical communication via an electrical circuit 128 with a source of illumination 108 contained in the first housing 120. The second housing 122 also has disposed on it a trigger 130, which is in operative communication with the camera 106 or circuit board 124 and is used to activate the camera 106 and the source of illumination.

The first housing 120 can have any desired shape (e.g., conical, cylindrical, cuboidal, and the like), but is preferably conical in shape and contains the source of illumination 108 that is disposed between the camera 106 and the substrate 102. The source of illumination 108 is disposed circumferentially along a portion of the first housing 120. It is generally disposed to be concentric around a lens of the camera 106. In one embodiment, an optional opaque shroud 160 is disposed around the system 100 to prevent any external light from causing distortions in the image collected by the camera 106. The opaque shroud 160 has an inner surface that is not reflective and has an opening through which the tube may be inserted for imaging and then removed.

The first housing 120 and the second housing 122 may be arranged in a manner so that the system 100 can be handheld and can easily be gripped and transported by hand. In one embodiment, the first housing 120 and the second housing 122 are part of the same piece of material. In other words, the system 100 is contained in a single housing. The housing is opaque to prevent light from distorting the image. The first housing 120 and the second housing are manufactured from any suitable material. In one embodiment the first housing 120 and the second housing 122 are manufactured from a light weight material such as a polymer, a ceramic or sheet metal. In an exemplary embodiment, the first housing 120 and the second housing 122 are manufactured from a polymer. It is desirable for the polymer to be opaque so as to minimize the amount of external light that can enter the system 100.

The camera 106 may be in electrical communication with the microprocessor (not shown) and the computer database (not shown). The electrical communication between the microprocessor and the database can include electrical hard wiring, wireless communication, or a combination thereof. The microprocessor and the computer database can be in communication with the internet. In an exemplary embodiment, the camera 106 is a digital camera with an image processing capability (i.e., it contains the microprocessor, which comprises an image processing library that is operative to process data obtained from images recorded by the camera). The image processing library is used to determine the center of mass of the tube, the inner diameter of the tube, the outer diameter of the tube, the out of roundness of the tube, the wall thickness, the area of flow, and the presence of flat spots on the inner diameter of the tube. The database stores data obtained from the microprocessor and can use the data to calculate the overall characteristics of the bend, such as the radius of the bend, the flow area across the bend, and the like. In one embodiment, the system 100 can comprise a monitor (not shown) for controlling the camera and for displaying an image of the tube cross-sectional area and other results. The monitor is in electrical communication with a computer that contains a data base for overall system control, annotations, data storage, reporting and network access, The camera 106 is used to image the cross-section of the linear tube (or bent tube) 104 that is disposed upon the substrate 102. The distance "l" from the camera to the surface of the substrate that contacts the cross-section of the bent tube is known and is used in measuring the dimensions of the tube. The camera 106 is provided with a means to maintain the camera at a fixed distance "l" from the substrate. This prevents variations in the magnification of the image due to variations in the value of "l".

The camera 106 is used to take a single image or a plurality of images of the cross-section of the tube and transmits these images to the microprocessor. In one embodiment, the camera 106 is used to take 1 to 12 images of each cross-sectional area of the tube. In an exemplary embodiment, the camera 106 is used to take a single image of the cross-section of the tube. This image is then processed in the microprocessor.

The optically transparent substrate 102 is used for positioning the tube whose properties are to be measured. It is desirable for the optically transparent substrate 102 upon which the tube 104 is mounted to have a transparency of greater than 75%, specifically greater than 85% and more specifically greater than 95%, based on the intensity of light that is incident upon the substrate 102. In one embodiment, the optically transparent substrate can transmit at least 75%, specifically at least 85% and more specifically at least 95% of the light that is incident upon it through it. The optically transparent substrate is fixedly attached to the first housing 120 and can be manufactured from an optically transparent material such as quartz, silica, alumina, titania, optically transparent polymers, and the like. Examples of optically transparent polymers that can be used are polystyrene, polycarbonate, polymethylmethacrylate, polycarbonate, polyester, polyetherimide, or the like, or a combination comprising at least one of the foregoing polymers. The optically transparent substrate 102 may be in the form of a flexible film or in the form of a solid rigid panel.

As noted above, the system 100 can optionally be housed in an opaque shroud 160, which functions to prevent external light from impinging on the camera 106 and distorting the collected image. The opaque case may be manufactured from wood, textile, metal, ceramics or polymers so long as the material prevents light from entering the camera 106.

The source of illumination 108 is preferably concentrically disposed around the camera 106 and is disposed along the periphery of the first housing 120 between the camera 106 and the optically transparent substrate 102. The source of illumination 108 can comprise a fluorescent source of illumination or can comprise light emitting diodes (LED) that are arranged in the form of a ring around the camera 106 and contacting the first housing 102. It is desirable to use a point source of illumination as the source of illumination to prevent image distortion because of multiple reflections. By using point sources of illumination, the cross-sectional area of the tube is effectively illuminated in a pattern designed to maximize the contrast on the edges of the cross-sectional area. The point source of illumination is arranged in the form of a ring around the camera. It is desirable to have the ring be concentrically arranged around the lens of the camera. In an exemplary embodiment, the point a source of illumination is a light emitting diode (LED).

The circuit board 124 and the battery pack 126 are disposed in the second housing 122 and are used to control the source of lighting 108. The circuit board 124 may also be used in lieu of a microprocessor. In other words, the circuit board 124 may contain imaging libraries. The trigger 130 is used to activate the camera 106 to capture an image of the cross-sectional area of the tube 104.

Figure 2:
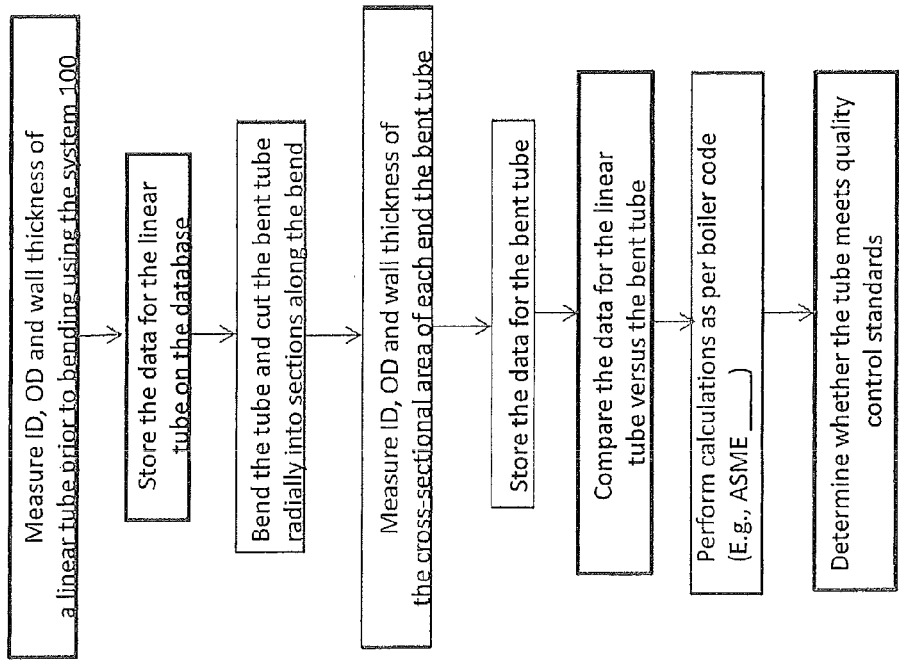
FIG. 2 depicts an exemplary method for measuring the dimensions and geometry of a bent tube.

The FIG. 2 represents an exemplary method of measuring the properties of a tube. In one embodiment, in one method of using the system, a cross-section of a tube is disposed upon a surface of the optically transparent substrate 102 and contacts it directly. The cross-section of a linear tube (i.e., an unbent straight tube) is first disposed upon the substrate 102 to determine its wall thickness and outer diameter. The camera 106 is operated to obtain an image of the cross-sectional area and this image is then used to compute the inner diameter, the outer diameter, wall thickness, the out of roundness, the length and area of any flat spots on the inner or outer circumference, the center of mass, and the like. These measurements and the computations resulting from these dimensions and geometrical features is then stored on the computer database. The protocol for obtaining these dimensions and geometrical features is detailed below in brief. If a series of unbent tubes are to be measured, these features can be calculated for each tube and stored on the computer database. If the tubes are subsequently bent, this data is used to compare with the data obtained on the bent tube. In one embodiment, it is used as a baseline for a comparison with bent tube sections.

These measurements can also be first made on a linear tube that is to be bent. When a bent tube is to be measured, the system 100 may be rotated so that the axis X-X' of the first housing 120 shown in the FIG. 1 is vertical. The measurements of the linear tube are first made and are stored to the database. Following this the tube is bent and measurements are made as detailed below. The bent portion of the tube 104 is cut into a plurality of sections and each section is disposed upon the transparent substrate 102. In one embodiment, the bent tube is cut into 2 to 10 sections, specifically 3 to 7 sections, and the opposing ends of each section is mounted on the optically transparent substrate to have its cross-sectional area imaged. The cross-sectional area is generally perpendicular to an axis that is parallel to the walls of the tube, where the axis passes through the center of the cross-sectional area. It is desirable, but not necessary for the tube to be arranged so that its center is concentric with the center of the camera 106 and the center of the source of illumination 108. In one embodiment, the tube is arranged so that the center of the cross-sectional area to be images lies on a single axis that includes the center of the camera 106 and the geometric center of the source of illumination 108. Upon mounting the tube 104 on the substrate with its cross-sectional area contacting the optically transparent substrate, an image of the cross-sectional area is taken by the camera and transmitted to the microprocessor, where it undergoes further processing as detailed below.

Following the capturing of the image of one end of the tube, a second image of the opposing end of the tube may be taken. For a linear tube, the second image is taken by transporting the hand held system to the opposite end of the tube and contacting it with the system 100 as shown in the FIG. 1. For a bent tube, when both ends of the first section are imaged, images of the second section may be captured, followed by images of the third section, and so on. In this manner, several cross-sectional area images of a linear tube or of a bent tube may be captured and transmitted to the microprocessor for additional computational processing. This additional processing is detailed below.

The cross-sectional image obtained by the camera 106 is divided (at both the inner diameter and the outer diameter) into a number of segments. The inner diameter and the outer diameter of the cross-section of the tube 104 are measured at each of these segments. In one embodiment, the cross-sectional image is divided from 2 to 288 segments, specifically from 24 to 144 segments, and more specifically from 48 to 96 segments. In an exemplary embodiment, the cross-sectional image is divided into 72 segments along both the inner diameter and the outer diameter.

The library in the microprocessor facilitates a computation of the average inner diameter and the average outer diameter for the cross-sectional image. It also calculates the out of roundness for the inner diameter and the outer diameter of the cross-sectional image and the resulting wall thickness. The microprocessor can also calculate and locate the area of flow within the inner diameter of the tube. It can also be used to calculate and locate the presence of any flat spots present on the inner surface area of the tube.

These computations can be made for multiple standards. In one embodiment, the computations can be made for ASME B31.1-2010 and EN 2 952-5.

The values calculated for the center of mass, the inner diameter, the outer diameter, the out of roundness, the wall thickness, area of flow, length and area of the maximum flat spot in the tube wall after bending, and the like are transmitted by the microprocessor to the computer database, where they are stored. Software programs stored on the computer database are used to calculate other statistical parameters of the tube (e.g., the radius of the bend, the fluid flow area, fluid flow volume, and the like).

In one embodiment, the database is operative to facilitate a comparison between the data obtained on the bent tube and that obtained on the linear (unbent) tube. The computer monitor can be used for displaying the image and calculated measurements for operator approval before performing any boiler code calculations. The system also permits the operator to select which boiler code the bent tube is expected to comply with. The system (i.e., the computer along with the associated database) permits performing calculations desired by any boiler code (including. but not limited to ASME B31.1-2010 and EN 2 952-5). The system is operative to compare the results of the boiler code calculations to the code limits to determine if each bent tube section passes or fails the code requirements.

In one embodiment, the system 100 may be used to detect imperfections in a plurality of tubes that are welded together to form a water-wall. Water-walls are generally manufactured by welding together a plurality of tubes as seen from the cross-sectional schematic diagram shown in the FIG. 3. With reference now to the FIG. 3, the water-wall comprises a plurality of tubes 204 that are welded to bars 208 by at least 4 weld beads. The tubes that are used in a water-wall generally have an outer diameter of 3 inches or smaller. Groups of tubes (often 6 to 12 at a time) are welded together with the separating bars on a special machine. Total water-wall width when fully assembled at the plant site is typically 40 to 60 feet and may include hundreds of tubes. Water-wall tubes are typically around 40 feet in length (shippable by truck or barge) before welding. The portable system 100 may be used to detect variations in tube spacing, missing weld beads and off-center bars as shown in the FIG. 3. Other water-wall problems detected could include incorrect tube diameter or wall thickness and twisted or missing connecting bars.

The system 100 disclosed herein has a number of advantages. In one embodiment, the system is operative to combine the calculated results from multiple tube cross-sections into an overall calculation for boiler code compliance for linear tubes or for bent tubes. The computer monitor permits the display and compiling of images of each tube cross-section, annotated with measurements and locations, into the inspection report. The computer database is operative to save all key measured and calculated data and this data can be stored, manipulated or summarized into a quality records database. The database can be used to generate an inspection report at any desired time and the contents of this report can be adapted depending on the requirements of the boiler code selected by the operator. The database is operative to provide the inspection report in a variety of different languages on command (examples being English, German, and Chinese languages). The inspection report can be generated in a variety of different formats (e.g., PDF, HTML, and the like). The computer database can also guide an operator who is not familiar with the boiler code compliance calculations through the process of taking all desired measurements and generating an inspection report.

When activated, the hand held system 100 captures an image of the tube end, calculates the tube diameter, maximum wall thickness, minimum wall thickness, average wall thickness and the out of roundness. The data may be displayed to the user on a dedicated display, for example, a LCD screen mounted on the outside of the system 100. Measurement data may also be transmitted to a computer using a wired connection (for example RS-232 serial, USB, or Ethernet) or may be transmitted wirelessly using a technology such as Bluetooth, Zigbee, or 802.11 WiFi. Data may also be stored internally on the measurement device for later transmission or analysis. For example, the device may calculate the maximum and minimum wall thickness measured from a batch of tubes, maximum and minimum diameters, and maximum, minimum, or average ovality.

Several other features make the handheld device faster and more convenient to use. A pistol grip and trigger button make it convenient for a user to carry the device and quickly measures multiple tubes in a group. An external display of the op or rear of the device provides quick feedback about the device status and recent measurements. Battery power and wireless connections make the device easier to handle by eliminating wires. The clear locating plate makes it easy to properly position the device for a measurement. Multiple measurements on a tube may be easily taken in two or three seconds using this device.

The system 100 is also physically advantageous in that it is portable and can be transported in a single hand to any site where testing of tubes is desired. In one embodiment system 100 weighs less than 10 pounds, specifically less than 5 pounds, and more specifically less than 3 pounds. It can be used to measure the cross-sectional properties of multiple tubes at a single time and can be used to measure properties of a water-wall that comprises a plurality of tubes.

The hand held system 100 can process the data from the image and provide the user with a print out on paper or can transfer data to a remote database where hard copies can be printed out or saved to a flash drive or to a compact disc.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A system for determining the quality of a tube, the system comprising:
   a housing having a grip to enable the housing to be held by a human being using a single hand;
   an optically transparent substrate disposed in the housing having a first side and an opposing second side;
   a camera disposed in the housing on the first side of the optically transparent substrate, wherein the camera is operative to capture an image of a cross-sectional area of the tube disposed against the second side of the optically transparent substrate;
   a source of illumination disposed in the housing in a ring on the periphery of the housing and located on the first side of the optically transparent substrate;
   wherein the source of illumination is operative to illuminate the cross-section of the tube disposed against the second side of the optically transparent substrate;
   a circuit board or microprocessor operative to process the image captured by the camera, wherein the circuit board or microprocessor is operative to calculate dimensions and geometry of the tube from the image and determine acceptance or rejection of the tube based on a parameter; and a battery pack disposed in the housing that is operative to supply electrical energy to the source of illumination and the circuit board or microprocessor.

2. The system of claim 1, further comprising a database in electrical communication with the circuit board or microprocessor.

3. The system of claim 1, wherein the circuit board or microprocessor are operative to calculate dimensions and geometry of the tube from the image and facilitate acceptance or rejection of the tube based upon a standard or a calibration chart.

4. The system of claim 1, further comprising a display attached to the housing for viewing measurements.

5. The system of claim 1, wherein the optically transparent substrate is selected from the group consisting of quartz, silica, alumina, titania, polystyrene, polycarbonate, polymethylmethacrylate, polycarbonate, polyester, polyetherimide, and a combination thereof.

6. The system of claim 1, wherein the source of illumination comprises a plurality of point sources of light arranged in a ring around the camera.

7. The system of claim 1, wherein the entire system is enclosed in an opaque shroud with an opening for introducing and removing the tube.

8. The system of claim 1, wherein the circuit board or microprocessor calculates and compiles results by measuring the inner diameter and outer diameter of a plurality of circumferential segments of the cross-section of the tube.

9. The system of claim 2, where the electrical communication comprises electrical hard wiring, wireless communication, or a combination thereof.

10. The system of claim 1, further comprising a trigger for activating the camera.

11. The system of claim 3, wherein the determining quality is in accordance with ASME B31.1-2010 and EN 2 952-5X.

12. The system of claim 1, wherein the circuit board or microprocessor comprises an image processing library for the tube.

13. The system of claim 8, wherein the circuit board or microprocessor computes at least a value selected from the group consisting of an inner diameter, an outer diameter, the wall thickness, an out of roundness of the tube, an area of flow, and a size of flat spots on an inner surface of the tube.

14. The system of claim 13, wherein the circuit board or microprocessor performs calculations required by a boiler code.

15. The system of claim 14, wherein the circuit board or microprocessor calculates and compiles results from a plurality of tube cross-sections into an overall calculation of boiler code compliance for the tube, which is bent.

16. The system of claim 1, wherein a portion of the housing has a shape selected from the group consisting of a conical shape, a cylindrical shape and a cuboidal shape.

* * * * *